(12) United States Patent
Muppidi et al.

(10) Patent No.: US 11,420,954 B2
(45) Date of Patent: Aug. 23, 2022

(54) PROCESS FOR THE SEPARATION OF GALLATED EPICATECHINS (EGCG AND ECG) FROM GREEN TEA EXTRACT OR GREEN TEA DUST

(71) Applicant: CRYSTALMORPHIX TECHNOLOGIES PVT. LTD, Hyberbad (IN)

(72) Inventors: Vamsee Krishna Muppidi, Hyderabad (IN); Satyanarayana Chinta, Hyderabad (IN)

(73) Assignee: Crystalmorphix Technologies Pvt. LTD, Hyderabad (IN)

( * ) Notice: Subject to any disclaimer, the term of this patent is extended or adjusted under 35 U.S.C. 154(b) by 178 days.

(21) Appl. No.: 16/769,853

(22) PCT Filed: Nov. 26, 2018

(86) PCT No.: PCT/IB2018/059285
§ 371 (c)(1),
(2) Date: Jun. 4, 2020

(87) PCT Pub. No.: WO2019/111093
PCT Pub. Date: Jun. 13, 2019

(65) Prior Publication Data
US 2021/0139446 A1    May 13, 2021

(30) Foreign Application Priority Data
Dec. 5, 2017    (IN) .............................. 201741043605

(51) Int. Cl.
C07D 311/62    (2006.01)
A61K 31/353    (2006.01)
A61K 36/82    (2006.01)

(52) U.S. Cl.
CPC .......... *C07D 311/62* (2013.01); *A61K 31/353* (2013.01); *A61K 36/82* (2013.01); *A61K 2236/333* (2013.01); *A61K 2236/51* (2013.01)

(58) Field of Classification Search
None
See application file for complete search history.

(56) References Cited

U.S. PATENT DOCUMENTS

| 4,248,789 A | 2/1981 | Okada |
| 4,613,672 A | 9/1986 | Hara |
| 4,913,909 A | 4/1990 | Hara et al. |
| 5,107,000 A | 4/1992 | Lunder |
| 6,210,679 B1 | 4/2001 | Bailey et al. |
| 6,214,868 B1 | 4/2001 | Ahn et al. |
| 7,312,199 B2 | 12/2007 | Burdick et al. |
| 9,018,248 B2 | 4/2015 | Shahidi et al. |
| 2010/0204204 A1 | 8/2010 | Zaworotko |

FOREIGN PATENT DOCUMENTS

| CN | 1136024 A | 11/1996 |
| CN | 1683363 A | 10/2005 |
| CN | 101381359 A | 3/2009 |
| CN | 102311419 A | 1/2012 |
| CN | 104557839 A | 4/2015 |
| CN | 105218503 A | 1/2016 |
| WO | 2007041891 A1 | 4/2007 |

OTHER PUBLICATIONS

International Search Report and Written Opinion of International Application No. PCT/IB2018/059285, dated Apr. 9, 2019, 9 pp.
International Preliminary Report on Patentability from International Application No. PCT/IB2018/059285, dated Jun. 18, 2020, 7 pp.

*Primary Examiner* — Michael Barker
(74) *Attorney, Agent, or Firm* — Shumaker & Sieffert, P.A.

(57) ABSTRACT

The present invention relates to an improved process for the separation of gallated epicatechins (EGCG & ECG) from green tea extract or green tea dust. The present invention specifically relates to an improved process for the separation of gallated epicatechins (EGCG & ECG) from green tea extract or green tea dust by forming hydrated gallated epicatechins (EGCG & ECG)-isonicotinic acid complex using isonicotinic acid as acid, organic solvents for liberating gallated epicatechins. The present invention more specifically relates to the process for the separation of gallated epicatechins (EGCG & ECG) from green tea extract or green tea dust, wherein processes comprises steps of dissolving, concentrating by centrifugation, adding, precipitating, filtering, slurrying, removing supernatant liquid, washing, extracting and freeze drying. The present invention also relates to hydrated gallated epicatechins (EGCG & ECG)-isonicotinic acid complex.

6 Claims, 11 Drawing Sheets

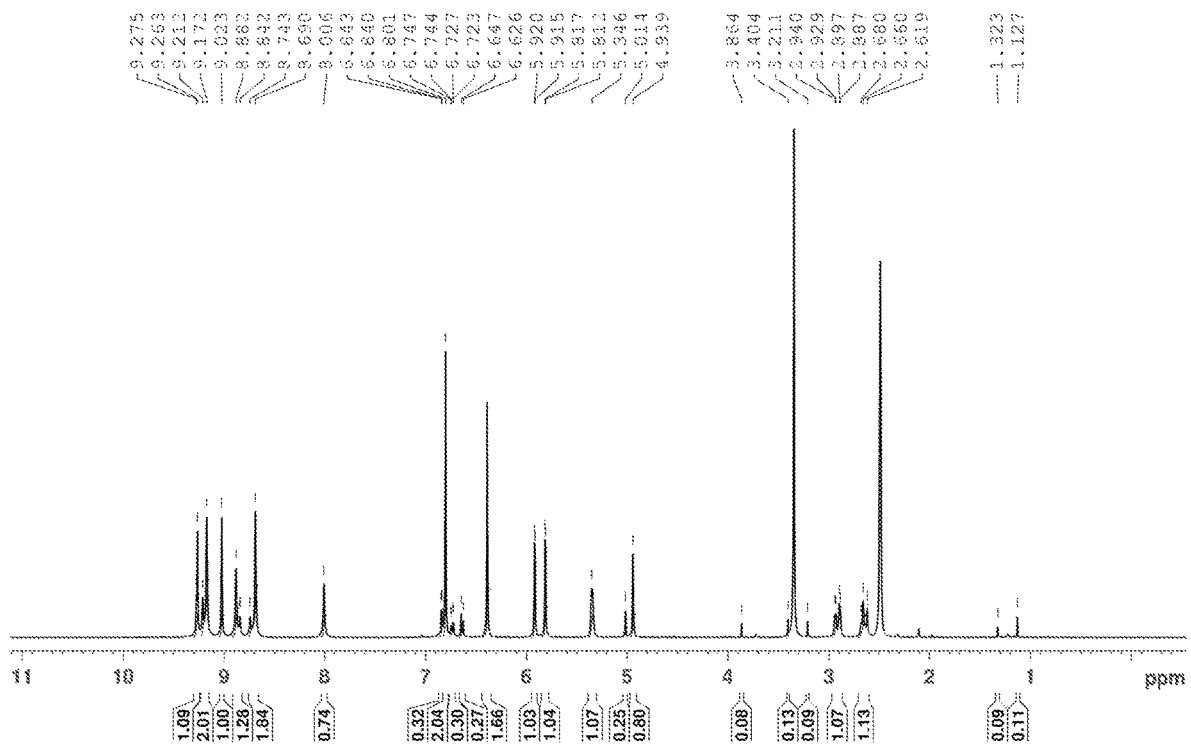

PROCESS FOR THE SEPARATION OF GALLATED EPICATECHINS (EGCG AND ECG) FROM GREEN TEA EXTRACT OR GREEN TEA DUST

This application is a national stage application under 35 U.S.C. § 371 of PCT Application No. PCT/IB2018/059285, filed Nov. 26, 2018, which claims the benefit of IN Application No. 201741043605 filed Dec. 05, 2017. The entire contents of each of PCT Application No. PCT/IB2018/059285 and IN Application No. 201741043605 are incorporated herein by reference in their entirety.

FIELD OF THE INVENTION

The present invention relates to an improved process for the separation of gallated epicatechins (EGCG & ECG) from green tea extract or green tea dust.

The present invention more particularly relates to an improved process for the separation of gallated epicatechins (EGCG & ECG) from green tea extract or green tea dust.

The present invention specifically relates to an improved process for the separation of gallated epicatechins (EGCG & ECG) from green tea extract or green tea dust by forming hydrated gallated epicatechins (EGCG & ECG)-isonicotinic acid complex using isonicotinic acid as acid, organic solvents for liberating gallated epicatechins.

The present invention more specifically relates to the process for the separation of gallated epicatechins (EGCG & ECG) from green tea extract or green tea dust, wherein processes comprises steps of dissolving, concentrating by centrifugation, adding, precipitating, filtering, slurrying, removing supernatant liquid, washing, extracting and freeze drying.

The present invention also relates to hydrated gallated epicatechins (EGCG & ECG)-isonicotinic acid complex.

BACKGROUND OF THE INVENTION

Green tea is a rich source of catechins, which account for about 30% of its dry weight. Green tea catechins are well known as antioxidants and their antioxidative properties were found to be stronger than those of vitamins C, vitamin E, and β-carotene. Green tea catechins are proposed to prevent cardiovascular diseases (CVD), microbial diseases, diabetes, and obesity. However, studies have revealed that the health benefits are only achieved when tea is consumed in sufficient amounts.

Green tea extract is defined as green tea polyphenol mixture isolated from *Camellia sinensis,* a plant native to Asia, with antiviral and antioxidant activities and potential chemopreventive activity and green tea dust is composed of fine grainy particles. This product is made solely from the leaves of the plant *Camellia Sinensis,* and it undergoes minimal oxidization during processing. This product is a greyish green colored granule powder like substance.

Catechins are comprised of a central 3-carbon unit, which is connected to two phenolic nuclei (two aromatic rings) with several hydroxyl groups. Tea catechins are classified into two groups: epistructured catechins and nonepistructured catechins. Epicatechins are the major catechins in tea, and epigallocatechin gallate (EGCG) accounts for the highest content, followed in decreasing order by epigallocatechin (EGC), epicatechin gallate (ECG), and epicatechin (EC). In contrast, nonepistructured catechins, including gallocatechin gallate (GCG), gallocatechin (GC), catechin gallate (CG) and catechin (C), are only present in small quantities in tea. A typical catechin profile in an extract from green tea leaf is comprised of 10-15% EGCG, 6-10% EGC, 2-3% ECG and 2% EC.

Among the major epicatechins, epigallocatechin (EGC) and epicatechin (EC) are non-gallated epicatechins and epigallocatechin gallate (EGCG) and epicatechin gallate (ECG) are gallated epicatechins. Gallated epicatechins (EGCG and ECG) are the most effective on suppressing inflammation, bacterial infection, tumor growth, and virus infection both in vitro and in vivo. They are capable of anti-oxidative, anti-carcinogenic, anti-diabetic, anti-obesity, anti-Alzheimer's disease, and anti-viral activities and can even serve as anticancer chemopreventive agents. In addition, they can even provide pronounced cardiovascular and metabolic health benefits.

Epigallocatechin gallate (EGCG) also known as epigallocatechin-3-gallate, is the ester of epigallocatechin and gallic acid, and is a type of catechin generally present in *Camellia sinensis* or the like. Epigallocatechin gallate (EGCG) is chemically represented as (2R,3R)-2-(3,4,5-trihydroxyphenyl)-3,4-dihydro-1 (2H)-benzopyran-3,5,7-triol-3-[3,4,5-trihydroxy benzonate). The chemical formula is $C_{22}H_{18}O_{11}$, the molecular weight is 458.37 g/mol and the structural formula is:

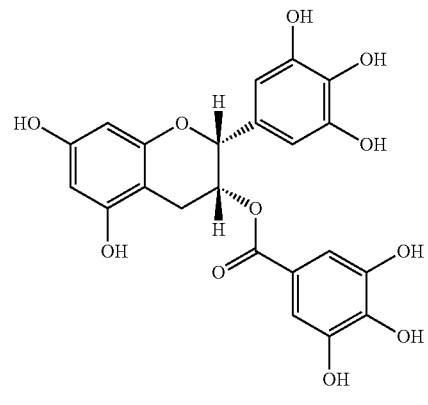

EGCG

Epicatechin gallate (ECG) is a flavan-3-ol, a type of flavonoid, present in green tea. Epicatechin gallate (ECG) is chemically represented as (2R,3R)-2-(3,4-Dihydroxyphenyl)-3,4-dihydro-1(2H)-benzopyran-3,5,7-triol-3-(3,4,5-trihydroxybenzoate)). The chemical formula is $C_{22}H_{18}O_{10}$, the molecular weight is 442.37 g/mol and the structural formula is:

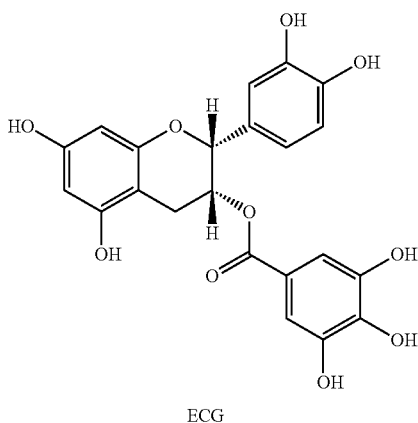 [SMILES: O=C(O[C@@H]1Cc2c(O)cc(O)cc2O[C@@H]1c1ccc(O)c(O)c1)c1cc(O)c(O)c(O)c1]

ECG

CN 1136024 discloses the preparation of monomeric catechin (EGCG, GCG and ECG) up to 98% purity using ethyl acetate-ethanol-water system as stationary phase and n-hexane-ethyl acetate-water system as mobile phase by high-speed counter current chromatography method from tea polyphenols crude.

CN 1683363 discloses isolation of catechins from green tea extract using 75% ethanol followed by removing caffeine using chloroform and separation by column chromatography to obtain pure catechin.

CN 101381359 discloses separation of pure EGCG and ECG from green tea extract using hot water extraction, precipitation with caffeine, chloroform and ethyl acetate extraction to form crude epigallocatechin gallate which is purified by silica gel column chromatography to obtain ECG and EGCG monomer.

CN 102311419 discloses purification of high content EGCG and low content of polyphenols raw material using Silica gel column chromatography.

CN 104557839 discloses process for the preparation of EGCG-Zn complex using EGCG and Zn-salts.

CN105218503 discloses preparation technology of tea catechins from fresh tea leaves.

U.S. Pat. No. 4,248,789 discloses process for producing catechins, characterized by adding an aqueous solution of caffeine to an aqueous solution of tannic substance to separate into a group of the free catechins and a group of the ester-type catechins, removing caffeine, and then fractionating each component of epicatechin, epigallocatechin, epicatechin gallate and epigallocatechin gallate with a distribution solvent on a column of Sephadex.

U.S. Pat. No. 4,613,672 discloses process for producing tea catechins comprising extracting tea leaves with hot water or an aqueous solution of methanol, ethanol or acetone, washing the extract containing solution with chloroform, transferring the washed solution into an organic solvent, removing the solution and passing the resulting solution through a reversed phase column in the presence of an eluting solution.

U.S. Pat. No. 4,913,909 discloses complex of a tea-leaf extract containing (−)-epigallocatechin gallate as the principal ingredient and active aluminum hydroxide.

U.S. Pat. No. 5,107,000 discloses process for obtaining catechin complexes from green tea using water, purified sea sand, dichloromethane and acetone.

U.S. Pat. No. 6,210,679 disclose isolation and purification of caffeine-free mixtures catechins from green tea leaves by four-step process to isolate highly pure, caffeine-free EGCG in high yields.

U.S. Pat. No. 7,312,199 discloses process for making (−)-epigallocatechin gallate (EGCG) by subjecting a green tea extract to chromatography on a macroporous polar resin, eluting EGCG from the resin with a polar elution and specific weight ranges of (−)-epigallocatechin gallate (EGCG), caffeine and epicatechin.

U.S. Pat. No. 9,018,248 discloses fatty acid derivatives of green tea catechins including epicatechin (EC), epicatechin gallate (ECG), epigallocatechin (EGC), epigallocatechin gallate (EGCG) and the process.

WO 2007/041891 discloses separation of catechins from green tea leaves by converting catechins into ester forms and converting back to the catechins.

US 2010/0204204 discloses hydrate of co-crystal of epigallocatechin gallate (EGCG) and isonicotinamide KA10153, its process, DSC, XRPD and single crystal x-ray diffraction data. It also discloses use of isonicotinamide and isonicotinic acid as co-crystal former. However, no specific preparation disclosure for cocrystal of epigallocatechin gallate (EGCG) and isonicotinic acid.

The prior art references hitherto reported discloses the separation of gallated epicatechins (EGCG & ECG) from crude tea polyphenol using high-speed counter current chromatographic separation method, from green tea extract using 75% ethanol followed by removing caffeine using chloroform and separation by column chromatography to obtain pure catechin and separation of gallated epicatechins (EGCG & ECG) from green tea using chromatographic techniques, solvent extraction, caffeine precipitation etc. None of the prior art reference discloses the use of isotonic acid for separating gallated epicatechins (EGCG & ECG) from green tea extract or green tea dust and formation of hydrated gallated epicatechins (EGCG & ECG)-isonicotinic acid complex from green tea extract or green tea dust.

It is therefore an object of the present invention to provide an improved process for the separation of gallated epicatechins (EGCG & ECG) from green tea extract and green tea dust by forming hydrated gallated epicatechins (EGCG & ECG)-isonicotinic acid complex using isonicotinic acid, which is high yielding and provides EGCG and ECG in better purity.

OBJECTIVE OF INVENTION

The main objective of the present invention is to provide an improved process for the separation of gallated epicatechins (EGCG & ECG) from green tea extract or green tea dust.

Still another objective of the present invention is to provide an improved process for the separation of gallated epicatechins (EGCG & ECG) from green tea extract or green tea dust.

Yet another objective of the present invention is to provide an improved process for the separation of gallated epicatechins (EGCG & ECG) from green tea extract and green tea dust by forming hydrated gallated epicatechins (EGCG & ECG)-isonicotinic acid complex, water miscible organic solvents for liberating gallated epicatechins, water immiscible solvents followed by treating with brine solution for removing insoluble materials.

Still yet another objective of the present invention is to provide an improved process for the separation of gallated epicatechins (EGCG & ECG) from green tea extract or green tea dust by forming hydrated gallated epicatechins (EGCG & ECG)-isonicotinic acid complex using isonicotinic acid as acid, ethanol or acetone or alcoholic as organic solvents for liberating gallated epicatechins and ethyl acetate with brine solution as water immiscible solvents for removing insoluble materials.

Yet another objective of the present invention is to provide an improved process for the separation of gallated epicatechins (EGCG & ECG) from green tea extract or green tea dust, wherein processes comprises steps of dissolving, concentrating by centrifugation, adding, precipitating, filtering, slurrying, removing supernatant liquid, washing, extracting and freeze drying.

SUMMARY OF INVENTION

Accordingly, the present invention provides an improved process for the separation of gallated epicatechins from green tea extract or green tea dust.

Another embodiment of the present invention provides an improved process for the separation of gallated epicatechins (EGCG & ECG) from green tea extract or green tea dust.

Yet another embodiment of the present invention provides an improved process for the separation of gallated epicatechins (EGCG & ECG) from green tea extract or green tea dust by forming hydrated gallated epicatechins (EGCG & ECG)-isonicotinic acid complex, water miscible organic solvents for liberating gallated epicatechins, water immiscible solvents followed by treating with brine solution for removing insoluble materials.

Yet another embodiment of the present invention provides an improved process for the separation of gallated epicatechins (EGCG & ECG) from green tea extract or green tea dust by forming hydrated gallated epicatechins (EGCG & ECG)-isonicotinic acid complex using isonicotinic acid as acid, ethanol or acetone or alcoholic as organic solvents for liberating gallated epicatechins and ethyl acetate water immiscible solvents for removing insoluble materials, followed by treatment with brine solution.

Still yet another embodiment of the present invention provides an improved process for the separation of gallated epicatechins (EGCG & ECG) from green tea extract or green tea dust, wherein processes comprises steps of dissolving, concentrating by centrifugation, adding, precipitating, filtering, slurrying, removing supernatant liquid, washing, extracting and freeze drying.

Still yet another embodiment of the present invention provides process for the separation of gallated epicatechins (EGCG & ECG) from green tea extract comprising:
a) providing a solution of green tea extract (>50% EGCG & >90% of Polyphenols) in water or organic solvents or mixtures thereof,
b) adding the isonicotinic acid to the solution obtained in step a),
c) keeping the solution with stirring to allow precipitation and slurried,
d) filtering the hydrated gallated epicatechins (EGCG & ECG)-isonicotinic acid complex,
e) slurrying the obtained hydrated gallated epicatechins (EGCG & ECG)-isonicotinic acid complex of step d) in water miscible organic solvent to liberate gallated epicatechins,
f) evaporating supernatant water miscible organic solvent of step e) to dryness under reduced pressure to obtain crude residue,
g) dissolving the crude residue of step f) in water immiscible solvent,
h) treating water immiscible solvent solution of step g) with brine solution and filtering off any trace level insoluble materials,
i) concentrating water immiscible solvent solution of step h) and adding small amount of water, distilling away the water immiscible solvent to obtain concentrated aqueous solution, and
j) freeze drying the concentrated aqueous solution of step i) to obtain >97% gallated epicatechins (>75% EGCG & >20% ECG).

Still yet another embodiment of the present invention provides process for the separation of gallated epicatechins (EGCG & ECG) from green tea dust comprising:
a) extracting green tea dust of any grade in water or aqueous acetone or aqueous alcoholic solution,
b) concentrating green tea dust of step a) to ¼ or preferably ⅕ of its original volume,
c) centrifuging the concentrated aqueous green extract solution to remove any insoluble materials,
d) adding the isonicotinic acid and hydrated gallated epicatechins (EGCG & ECG)-isonicotinic acid complex seed material to the solution obtained in step c),
e) keeping the solution with stirring to allow further precipitation and slurried,
f) filtering the crude hydrated gallated epicatechins (EGCG & ECG)-isonicotinic acid complex,
g) slurrying the obtained crude hydrated gallated epicatechins (EGCG & ECG)-isonicotinic acid complex of step f) in water immiscible solvent and filtering,
h) slurrying the obtained partially purified hydrated gallated epicatechins (EGCG & ECG)-isonicotinic acid complex of step g) in water miscible organic solvent to liberate gallated epicatechins,
i) evaporating supernatant water miscible organic solvent of step h) to dryness under reduced pressure to obtain crude residue,
j) dissolving the crude residue of step i) in water immiscible solvent,
k) treating water immiscible solvent solution of step j) with brine solution and filtering off any trace level insoluble materials,
l) concentrating water immiscible solvent solution of step k) and adding small amount of water, distilling away the water immiscible solvent to obtain concentrated aqueous solution, and
m) freeze drying the concentrated aqueous solution of step l) to obtain >97% gallated epicatechins (>75% EGCG & >20% ECG).

Yet another embodiment of the present invention provides hydrated gallated epicatechins (EGCG & ECG) isonicotinic acid complex from green extract characterized by a XRPD pattern having peaks located at about 6.010, 6.612, 7.258, 11.646, 12.294, 14.610, 14.939, 19.229, 22.032, 26.188, 26.934, 27.433, 29.522±0.2 °2θ.

Yet another embodiment of the present invention provides crude hydrated gallated epicatechins (EGCG & ECG)-isonicotinic acid complex from green tea dust is characterized by a XRPD pattern having peaks located at about 5.995, 6.620, 7.227, 11.656, 12.268, 14.637, 14.824, 16.569*, 19.383, 22.007, 26.14, 26.914, 27.481, 27.821*, 29.489±0.2 °2θ. (* Isonicotinic acid phase contamination peaks).

BRIEF DESCRIPTION OF THE FIGURES

FIG. 11 shows $^1$H NMR of gallated epicatechins (EGCG & ECG) obtained from green tea dust.

DETAILED DESCRIPTION OF THE INVENTION

Figure 1:
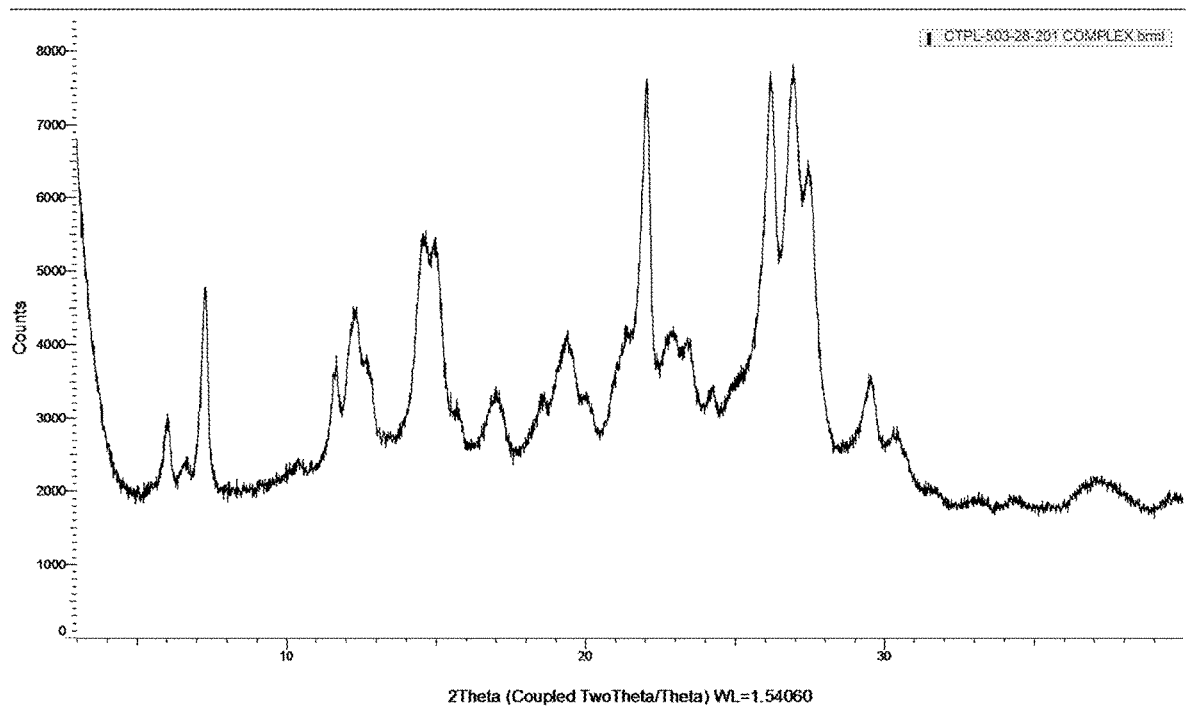
FIG. 1 shows XPRD pattern of hydrated gallated epicatechins (EGCG & ECG) isonicotinic acid complex obtained from green tea extract (>50% EGCG & >90% of Polyphenols).

Accordingly, the present invention provides an an improved process for the separation of gallated epicatechins from green tea extract and green tea dust.

The present invention provides an improved process for the separation of gallated epicatechins (EGCG & ECG) from green tea extract or green tea dust.

The present invention also provides an improved process for the separation of gallated epicatechins (EGCG & ECG) from green tea extract or green tea dust by forming hydrated gallated epicatechins (EGCG & ECG)-isonicotinic acid complex, water miscible organic solvents for liberating gallated epicatechins, water immiscible solvents followed by treating with brine solution for removing insoluble materials.

Water miscible organic solvents that may be used in the present invention include, but are not limited to alcohols such as methanol, ethanol, 1-propanol, 2-propanol, t-butyl alcohol and the like; ketones such as acetone, methyl butyl ketone and the like; ethers such as tetrahydrofuran, 1,4-dioxane and the like; and any mixtures thereof. Preferably used organic solvents are ethanol or acetone.

Water immiscible solvents of the present invention includes but not limited to ethyl acetate, propyl acetate, butyl acetate, diethyl ether, dichloromethane and chloroform. Preferably used water immiscible solvent is ethyl acetate.

Gallated epicatechins (EGCG & ECG) are separated from green tea extract or green tea dust by forming hydrated gallated epicatechins (EGCG & ECG)-isonicotinic acid complex using isonicotinic acid as acid, ethanol or acetone or alcoholic as organic solvents for liberating gallated epicatechins and ethyl acetate as water immiscible solvents followed by treating with brine solution for removing insoluble materials.

Separation process of gallated epicatechins from green tea extract and green tea dust includes steps of dissolving, concentrating by centrifugation, adding, precipitating, filtering, slurrying, removing supernatant liquid, washing, extracting and freeze drying.

The present invention provides process for the separation of gallated epicatechins EGCG & ECG from green tea extract comprising:
a) providing a solution of green tea extract (>50% EGCG & >90% of Polyphenols) in water or organic solvents or mixtures thereof,
b) adding the isonicotinic acid to the concentrated solution obtained in step a),
c) keeping the solution with stirring to allow precipitation and slurried for 12 hrs,
d) filtering the hydrated gallated epicatechins (EGCG & ECG)-isonicotinic acid complex,
e) slurrying the obtained hydrated gallated epicatechins (EGCG & ECG)-acid complex of step d) in water miscible organic solvents to liberate gallated epicatechins,
f) evaporating supernatant water miscible organic solvent of step e) to dryness under reduced pressure to obtain crude residue,
g) dissolving crude residue of step f) in water immiscible solvent,
h) treating water immiscible solvent solution of step g) three times with brine solution and filtering off any trace level insoluble materials,
i) concentrating water immiscible solvent solution of step h) and adding small amount of water, distilling away the water immiscible solvent to obtain concentrated aqueous solution, and
j) freeze drying the concentrated aqueous solution of step i) to obtain >97% gallated epicatechins (>75% EGCG & >20% ECG).

The present invention provides process for the separation of gallated epicatechins (EGCG & ECG) from green tea dust comprising:
a) extracting green tea dust of any grade in water or aqueous acetone or aqueous alcoholic solution ,
b) concentrating green tea dust of step a) to ¼ or preferably ⅕ of its original volume,
c) centrifuging the concentrated aqueous green extract solution to remove any insoluble materials,
d) adding the isonicotinic acid and hydrated gallated epicatechins (EGCG & ECG)-isonicotinic acid complex seed material to the solution obtained in step c),
e) keeping the solution with stirring to allow further precipitation and slurried,
f) filtering the crude hydrated gallated epicatechins (EGCG & ECG)-isonicotinic acid complex,
g) slurrying the obtained crude hydrated gallated epicatechins (EGCG & ECG)-isonicotinic acid complex of step f) in water immiscible solvent and filtering,
h) slurrying the obtained partially purified hydrated gallated epicatechins (EGCG & ECG)-isonicotinic acid complex of step g) in water miscible organic solvent to liberate gallated epicatechins,
i) evaporating supernatant water miscible organic solvent of step h) to dryness under reduced pressure to obtain crude residue,
j) dissolving the crude residue of step i) in water immiscible solvent, k) treating water immiscible solvent solution of step j) with brine solution and filtering off any trace level insoluble materials, l) concentrating water immiscible solvent solution of step k) and adding small amount of water, distilling away the water immiscible solvent to obtain concentrated aqueous solution, and m) freeze drying the concentrated aqueous solution of step l) to obtain >97% gallated epicatechins (>75% EGCG & >20% ECG).

Green tea extract of the present invention can be obtained by dissolving green tea extract (>50% EGCG & >90% of Polyphenols) in water or green tea dust in water or aqueous alcoholic solution, concentrating the aqueous extract to ¼ or preferably ⅕ of its original volume and centrifuging to remove any insoluble materials.

Hydrated gallated epicatechins (EGCG & ECG)-isonicotinic acid complex of the present invention, if required, can be slurried in ethyl acetate preferably at 50° C. to remove impurities like EGC, EC and caffeine etc The obtained hydrated gallated epicatechins (EGCG & ECG)-isonicotinic acid complex from green tea extract is characterized by a XRPD pattern having peaks located at about 6.010, 6.612, 7.258, 11.646, 12.294, 14.610, 14.939, 19.229, 22.032, 26.188, 26.934, 27.433, 29.522±0.2 °2θ (FIG. 1).

Figure 2:
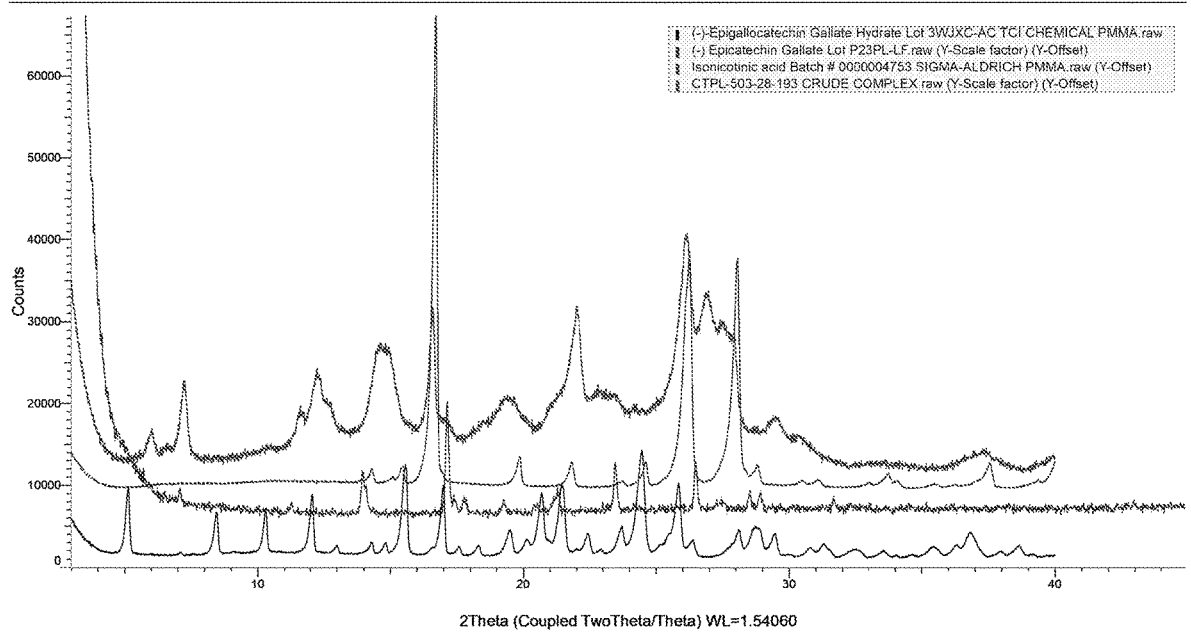
FIG. 2 shows XPRD pattern of overlay of: (a) EGCG hydrate (b) ECG (c) Isonicotinic acid (d) hydrated gallated epicatechins (EGCG & ECG) isonicotinic acid complex obtained from green tea extract (>50% EGCG & >90% of Polyphenols) (bottom to top).

Gallated epicatechins obtained by the process of the present invention is confirmed by XRPD overlay of: (a) EGCG hydrate (b) ECG (c) Isonicotinic acid (d) hydrated gallated epicatechins (EGCG & ECG) isonicotinic acid complex obtained from green tea extract (>50% EGCG & >90% of Polyphenols) (bottom to top) using ethanol (FIG. 2).

Figure 3:
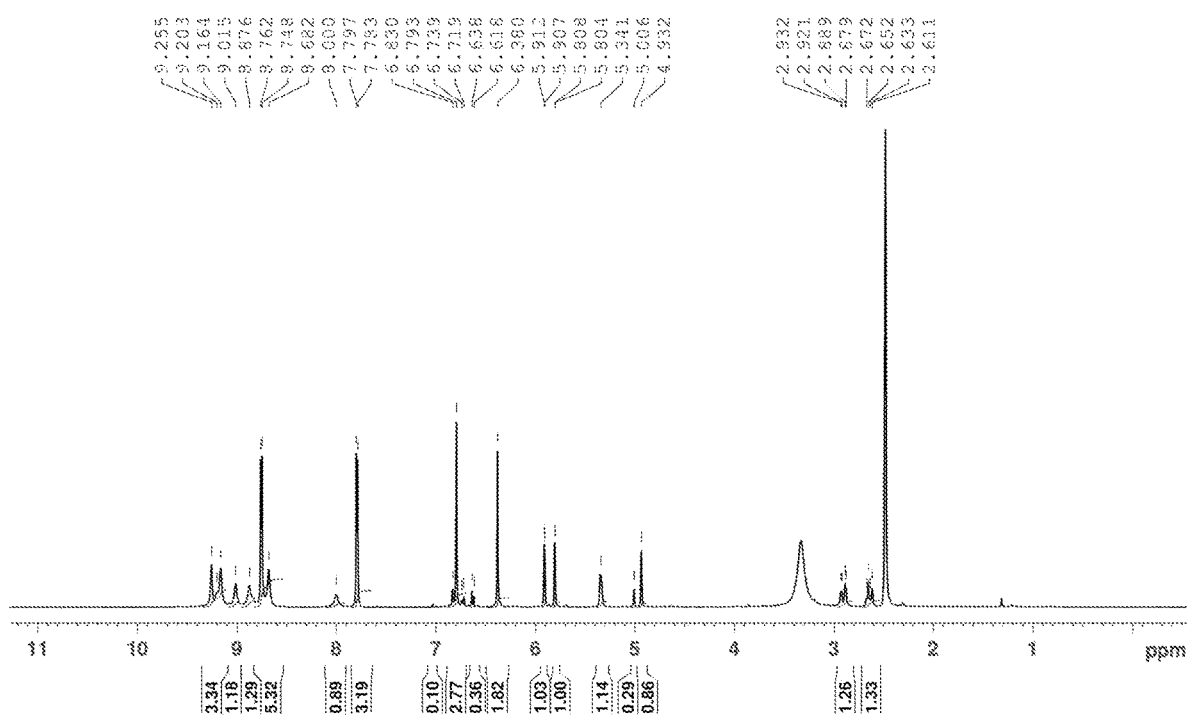
FIG. 3 shows $^1$H NMR of hydrated gallated epicatechins (EGCG & ECG) isonicotinic acid complex obtained from green tea extract (>50% EGCG & >90% of Polyphenols).

The obtained hydrated gallated epicatechins (EGCG & ECG)-isonicotinic acid complex from green tea extract (>50% EGCG & >90% of Polyphenols) is confirmed by proton NMR (FIG. 3).

Figure 4:
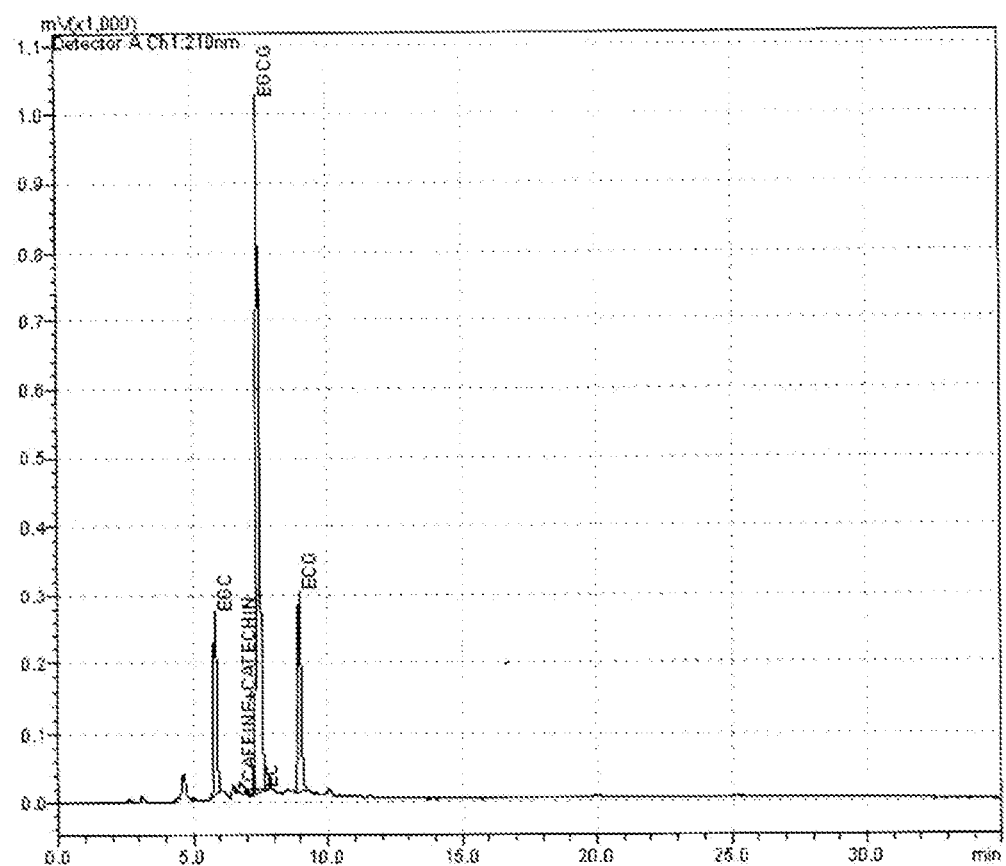
FIG. 4 shows HPLC of input green tea extract (>50% EGCG & >90% of Polyphenols.

Green tea extract (>50% EGCG & >90% of Polyphenols) containing EGCG, Caffeine+catechin, EGCG, EC, ECG is confirmed by HPLC chromatogram (FIG. 4).

Figure 5:
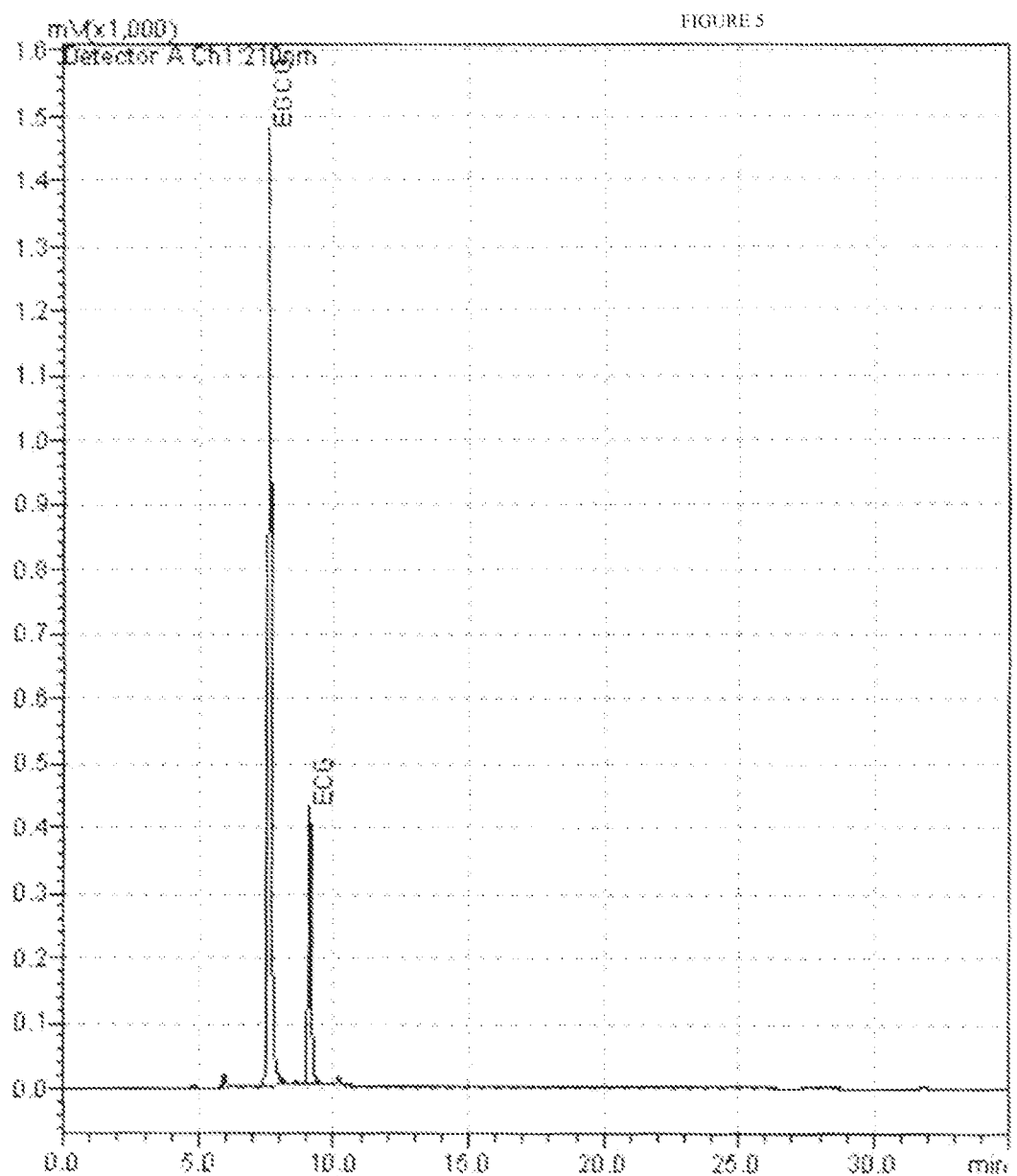
FIG. 5 shows HPLC of gallated epicatechins (EGCG & ECG) obtained from green tea extract (>50% EGCG & >90% of Polyphenols).

HPLC showing the presence of gallated epicatechins (EGCG & ECG) obtained from green tea extract (>50% EGCG & >90% of Polyphenols) indicates purity of EGCG (75.744%), ECG (21.310%) (>97% gallated epicatechins (EGCG & ECG)) (FIG. 5).

Figure 6:
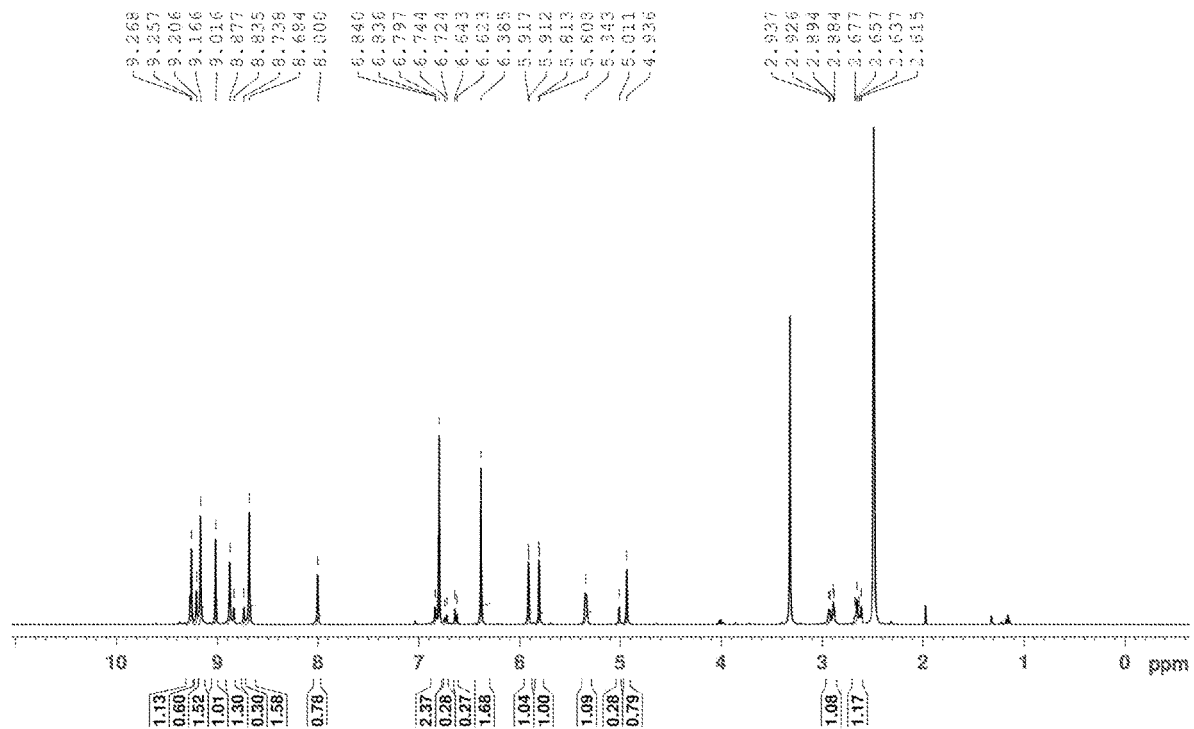
FIG. 6 shows 1H NMR of gallated epicatechins (EGCG & ECG) obtained from green tea extract (>50% EGCG & >90% of Polyphenols).

The obtained gallated epicatechins (EGCG & ECG) from green tea extract (>50% EGCG & >90% of Polyphenols) using ethanol is confirmed by proton NMR (FIG. 6).

Figure 7:
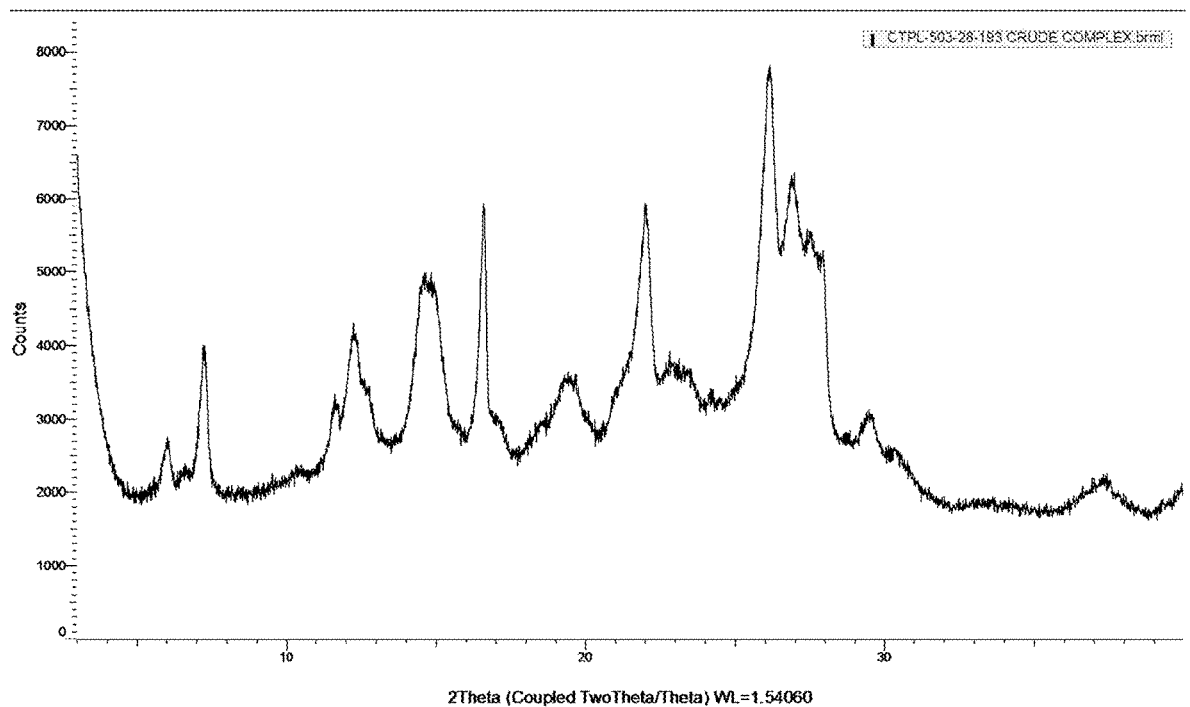
FIG. 7 shows XPRD pattern of crude hydrated gallated epicatechins (EGCG & ECG) isonicotinic acid complex obtained from green tea dust.

The obtained crude hydrated gallated epicatechins (EGCG & ECG)-isonicotinic acid complex from green tea dust is characterized by a XRPD pattern having peaks located at about 5.995, 6.620, 7.227, 11.656, 12.268, 14.637, 14.824, 16.569*, 19.383, 22.007, 26.14, 26.914, 27.481, 27.821*, 29.489±0.2 °2θ (* Isonicotinic acid phase contamination peaks) (FIG. 7).

Figure 8:
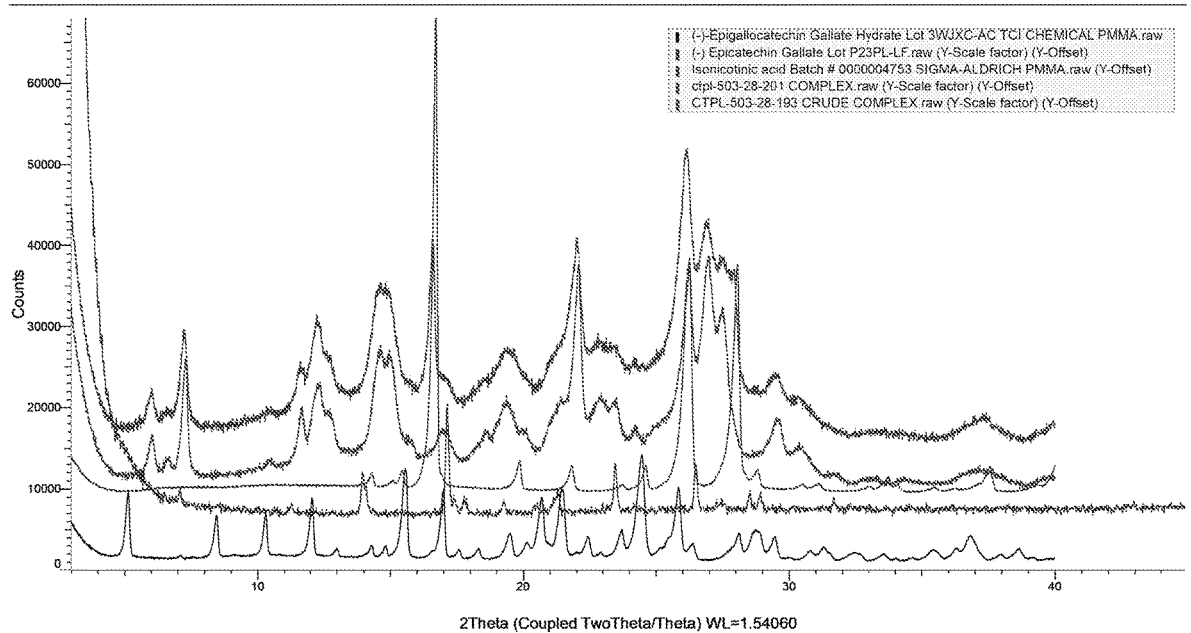
FIG. 8 shows XPRD overlay of: (a) EGCG hydrate (b) ECG (c) Isonicotinic acid (d) hydrated gallated epicatechins (EGCG & ECG) isonicotinic acid complex obtained from green tea extract (>50% EGCG & >90% of Polyphenols) (e) crude hydrated gallated epicatechins (EGCG & ECG) isonicotinic acid complex obtained from green tea dust (bottom to top).

Gallated epicatechins obtained by the process of the present invention is confirmed by XRPD overlay of: (a) EGCG hydrate (b) ECG (c) Isonicotinic acid (d) hydrated gallated epicatechins (EGCG & ECG) isonicotinic acid complex obtained from green tea extract (>50% EGCG & >90% of Polyphenols) (e) crude hydrated gallated epicatechins (EGCG & ECG) isonicotinic acid complex obtained from green tea dust (bottom to top) (FIG. 8).

Figure 9:
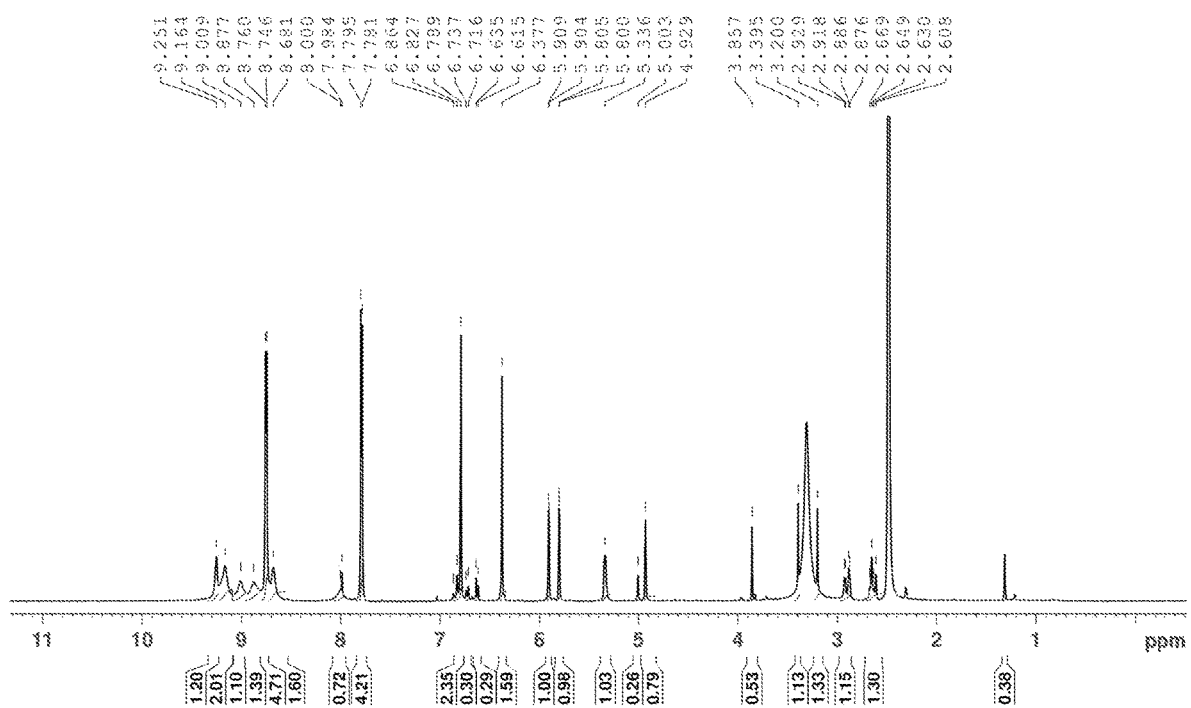
FIG. 9 shows $^1$H NMR of crude hydrated gallated epicatechins (EGCG & ECG) isonicotinic acid complex obtained from green tea dust.

The obtained crude hydrated gallated epicatechins (EGCG & ECG)-isonicotinic acid complex from green tea dust is confirmed by proton NMR (FIG. 9).

Figure 10:
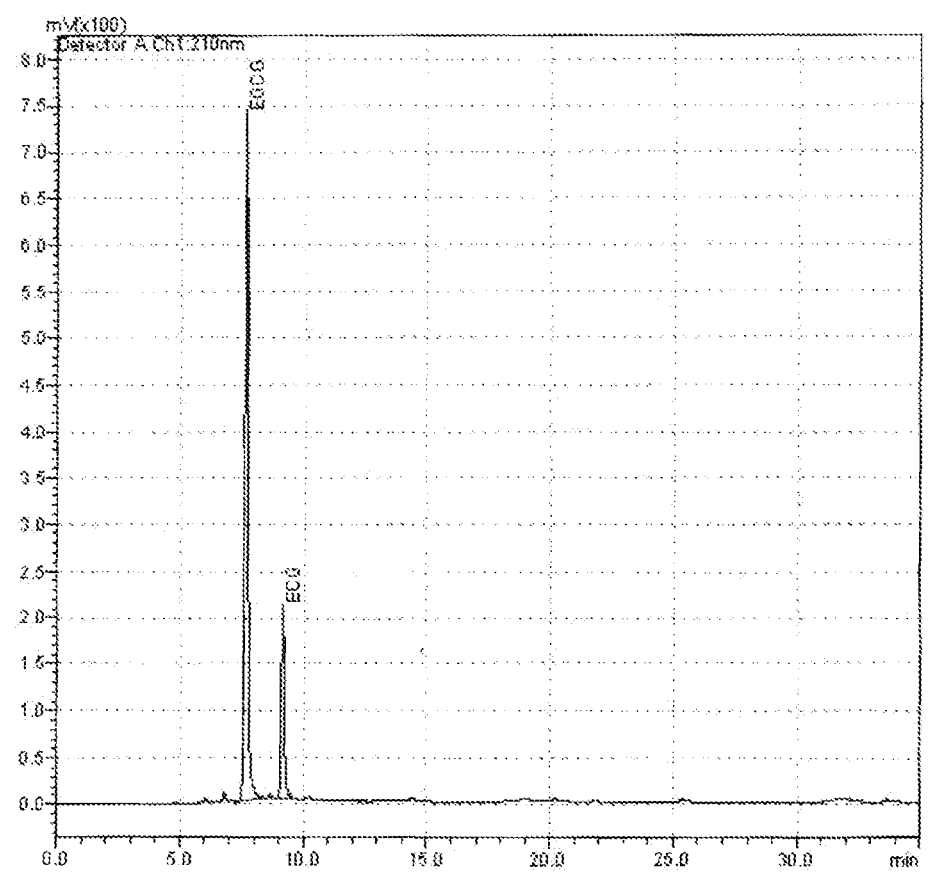
FIG. 10 shows HPLC of gallated epicatechins (EGCG & ECG) obtained from green tea dust.

HPLC showing the presence of pure gallated epicatechins (EGCG & ECG) obtained from green tea dust indicates purity of EGCG (76.801%), ECG (20.788%) (>97% gallated epicatechins (EGCG & ECG)) (FIG. 10).

The obtained gallated catechin (EGCG & ECG) from green tea dust is confirmed by proton NMR (FIG. 11).

The present invention is further illustrated by the following examples which are provided merely to be exemplary of the inventions and is not intended to limit the scope of the invention. Certain modifications and equivalents will be apparent to those skilled in the art and are intended to be included within the scope of the present invention.

EXAMPLES

Process for Production of Galloyl or Gallated Epicatechins (EGCG & ECG) from Green Tea Extract (>50% EGCG & >90% of Polyphenols):

Example 1

Step 1: Preparation of Hydrated Gallated Epicatechins (EGCG & ECG) Isonicotinic Acid Complex:

10 grams of green tea extract (>50% EGCG & >90% of Polyphenols) was dissolved in 80 ml of water at room temperature. To this clear solution, 3.02 grams of isonicotinic acid was added and precipitation observed after an hour and the slurry continued for 12 hrs. Filtered the hydrated gallated epicatechins (EGCG & ECG)-isonicotinic acid complex and washed the wet cake with 80 ml of water and suck dried. The hydrated gallated epicatechins (EGCG & ECG)-isonicotinic acid complex was grinded using mortar pistil to obtain 8.7 grams of fine powder.

Step 2: Breaking Hydrated Gallated Epicatechins (EGCG & ECG) Isonicotinic Acid Complex to Liberate Gallated Epicatechins 42.5 ml of ethanol is added to 8.5 grams of hydrated gallated epicatechins (EGCG & ECG)-isonicotinic acid complex and the suspension slurried at 45° C. for 1 hr. Filtered the precipitate using 0.45 micron filter and washed with 3 ml of ethanol. Precipitation characterized as isonicotinic acid. The gallated catechin (EGCG & ECG) containing ethanol solution was evaporated at 45° C. under reduced pressure to give crude residue. Then the crude residue dissolved in 42.5 ml of ethyl acetate. The ethyl acetate solution was treated three times with each 28.3 ml of brine solution to remove water content. Insoluble particles observed at junction. Filtered the ethyl acetate solution using 0.45 μm filter and the solution was concentrated under reduced pressure. After addition of a small amount of water, the ethyl acetate was distilled away to obtain a concentrated aqueous solution. This concentrated aqueous solution was then freeze dried to obtain 5.3 grams of gallated epicatechins (EGCG & ECG) with purity ≥97% and it comprise ≥75% of EGCG.

Example 2

Step-1: Preparation of Hydrated Gallated Epicatechins (EGCG & ECG) Isonicotinic Acid Complex:

10 grams of green tea extract (>50% EGCG & >90% of Polyphenols) was dissolved in 80 ml of water at room temperature. To this clear solution, 3.02 grams of isonicotinic acid was added and precipitation observed after an hour and the slurry continued for 12 hrs. Filtered the hydrated gallated epicatechins (EGCG & ECG)-isonicotinic acid complex and washed the wet cake with 80 ml of water and suck dried. The hydrated gallated epicatechins (EGCG & ECG)-isonicotinic acid complex was grinded using mortar pistil to obtain 8.7 grams of fine powder.

Step 2: Breaking Hydrated Gallated Epicatechins (EGCG & ECG) Isonicotinic Acid Complex to Liberate Gallated Epicatechins 42.5 ml of acetone is added to 8.5 grams of hydrated gallated epicatechins (EGCG & ECG) -isonicotinic acid complex and the suspension slurried at 45° C. for 1 hr. Filtered the precipitate using 0.45 micron filter and washed with 3 ml of acetone. Precipitation characterized as isonicotinic acid. The gallated catechin (EGCG & ECG) containing acetone solution was evaporated at 45° C. under reduced pressure to give crude residue. Then the crude residue dissolved in 42.5 ml of ethyl acetate. The ethyl acetate solution was treated three times with each 28.3 ml of brine solution to remove water content. Insoluble particles observed at junction. Filtered the ethyl acetate solution using 0.45 µm filter and the solution was concentrated under reduced pressure. After addition of a small amount of water, the ethyl acetate was distilled away to obtain a concentrated aqueous solution. This concentrated aqueous solution was then freeze dried to obtain 5.5 grams of gallated epicatechins (EGCG & ECG) with purity ≥97% and it comprise ≥75% of EGCG.

Process for Production of Galloyl or Gallated Epicatechins (EGCG & ECG) from Green Tea Dust:

Example 3

Step 1: Process to Obtain Crude Hydrated Gallated Epicatechins (EGCG & ECG) Isonicotinic Acid Complex 60 grams of green tea dust were extracted with 450 ml of aqueous acetone (acetone:water ratio 2:1) (tea: solvent ratio 1:7.5) at 50° C. for 3 hrs. Insoluble material filtered off. The supernatant green tea extract solution concentrated to 90 ml under reduced pressure at 40° C., then the concentrated aqueous solution centrifuged at 25° C. for 10 min (7000 rpm) to remove any insoluble materials. 3.999 grams of isonicotinic acid and 0.540 grams of hydrated gallated epicatechins (EGCG & ECG)-isonicotinic acid complex seed material were added to above clear solution and the precipitation observed after an hour and the slurry continued for 12 hrs. Filtered the crude hydrated gallated epicatechins (EGCG & ECG)-isonicotinic acid complex and washed the wet cake with 90 ml of water and suck dried. The crude complex was grinded using mortar pistil to obtain 9.24 grams of fine powder. The material characterized as crude hydrated gallated epicatechins (EGCG & ECG)-isonicotinic acid complex (mixture of hydrated gallated epicatechins (EGCG & ECG)-isonicotinic acid complex and isonicotinic acid).

Step 2: Breaking Crude Hydrated Gallated Epicatechins (EGCG & ECG) Isonicotinic Acid Complex to Obtain Gallated Epicatechins 8.7 grams of crude hydrated gallated epicatechins (EGCG & ECG)-isonicotinic acid complex was suspended in 174 ml of ethyl acetate and slurried at 50° C. for 2 hrs. Filtered the partially purified complex. 35 ml of acetone added to 7 grams of partially purified hydrated gallated epicatechins (EGCG & ECG) isonicotinic acid complex and the suspension slurried at 45° C. for 1 hr. Filtered the precipitate using 0.45 micron filter and washed with 3 ml of acetone. Precipitation characterized as isonicotinic acid. The gallated catechin (EGCG & ECG) containing acetone solution was evaporated at 45° C. under reduced pressure to give crude residue. Then the crude residue dissolved in 35 ml of ethyl acetate. The ethyl acetate solution was treated three times with each 23.3 ml of brine solution to remove water content. Insoluble particles observed at junction. Filtered the ethyl acetate solution using 0.45 µm filter and the solution was concentrated under reduced pressure. After addition of a small amount of water, the ethyl acetate was distilled away to obtain a concentrated aqueous solution. This concentrated aqueous solution was then freeze dried to obtain 3.4 grams of gallated epicatechins (EGCG & ECG) with purity ≥97% and it comprise ≥75% of EGCG.

Example 4

Step 1: Process to Obtain Crude Hydrated Gallated Epicatechins (EGCG & ECG) Isonicotinic Acid Complex 60 grams of green tea dust were extracted with 600 ml of aqueous ethanol (ethanol:water ratio 1:1) (tea: solvent ratio 1:10) at 50° C. for 3 hrs. Insoluble material filtered off. The supernatant green tea extract solution concentrated to 90 ml under reduced pressure at 40° C., then the concentrated aqueous solution centrifuged at 25° C. for 10 min (7000 rpm) to remove any insoluble materials. 4 grams of isonicotinic acid and 0.540 grams of hydrated galloyl catechins (EGCG & ECG)-isonicotinic acid complex seed material were added to above clear solution and the precipitation observed after an hour and the slurry continued for 12 hrs. Filtered the crude hydrated galloyl catechins (EGCG & ECG)-isonicotinic acid Complex and washed the wet cake with 90 ml of water and suck dried. The crude complex was grinded using mortar pistil to obtain 7.6 gms of fine powder. The material characterized as crude hydrated gallated epicatechins (EGCG & ECG)-isonicotinic acid complex (mixture of hydrated gallated epicatechins (EGCG & ECG)-isonicotinic acid complex and isonicotinic acid).

Step 2: Breaking Crude Hydrated Gallated Epicatechins (EGCG & ECG) Isonicotinic Acid Complex to Obtain Gallated Epicatechins 7 grams of crude hydrated galloyl catechins (EGCG & ECG)-isonicotinic acid complex-1 was suspended in 140 ml of ethyl acetate and slurried at 50° C. for 2 hrs. Filtered the partially purified complex. 25 ml of ethanol added to 5 grams of partially purified hydrated galloyl catechins (EGCG & ECG) isonicotinic acid complex and the suspension slurried at 45° C. for 1 hr. Filtered the precipitate using 0.45 micron filter and washed with 3 ml of ethanol. Precipitation characterized as isonicotinic acid. The galloyl catechin (EGCG & ECG) containing ethanol solution was evaporated at 45° C. under reduced pressure to give crude residue. Then the crude residue dissolved in 25 ml of ethyl acetate. The ethyl acetate solution was treated three times with each 16.6 ml of brine solution to remove water content. Insoluble particles observed at junction. Filtered the ethyl acetate solution using 0.45 µm filter and the solution was concentrated under reduced pressure. After addition of a small amount of water, the ethyl acetate was distilled away to obtain a concentrated aqueous solution. This concentrated aqueous solution was then freeze dried to obtain 2.3 grams of galloyl catechins (EGCG & ECG) with purity ≥97% and it comprise ≥75% of EGCG.

We claim:

1. A process for separation of gallated epicatechins (EGCG & ECG) from green tea extract or green tea dust, wherein the process comprises:
   a) forming hydrated gallated epicatechins (EGCG & ECG)-isonicotinic acid complex,
   b) liberating gallated epicatechins with water miscible organic solvents, and c) removing insoluble materials with water immiscible solvents followed by brine solution.

2. The process of claim 1, the process further comprising:
a) providing a solution of green tea extract (>50% EGCG & >90% of Polyphenols) in water or organic solvents or mixtures thereof,
b) adding isonicotinic acid to the concentrated solution obtained in step a),
c) keeping the solution with stirring to allow precipitation and slurried for 12 hrs,
d) filtering to obtain hydrated gallated epicatechins (EGCG & ECG)-isonicotinic acid complex,
e) slurrying the obtained hydrated gallated epicatechins (EGCG & ECG)-acid complex of step d) in water miscible organic solvents to liberate gallated epicatechins,
f) evaporating supernatant water miscible organic solvent of step e) to dryness under reduced pressure to obtain crude residue,
g) dissolving crude residue of step f) in water immiscible solvent,
h) treating water immiscible solvent solution of step g) three times with brine solution and filtering off any trace level insoluble materials,
i) concentrating water immiscible solvent solution of step h) and adding small amount of water, distilling away the water immiscible solvent to obtain concentrated aqueous solution, and
j) freeze drying the concentrated aqueous solution of step i) to obtain >97% gallated epicatechins (>75% EGCG & >20% ECG).

3. The process of claim 1, the process further comprising:
a) extracting green tea dust of any grade in water or aqueous acetone or aqueous alcoholic solution,
b) concentrating green tea dust of step a) to ¼ or preferably ⅕ of its original volume,
c) centrifuging the concentrated aqueous green extract solution to remove any insoluble materials,
d) adding isonicotinic acid and hydrated gallated epicatechins (EGCG & ECG)-isonicotinic acid complex seed material to the solution obtained in step c),
e) keeping the solution with stirring to allow further precipitation and slurried,
f) filtering to obtain crude hydrated gallated epicatechins (EGCG & ECG)-isonicotinic acid complex,
g) slurrying the obtained crude hydrated gallated epicatechins (EGCG & ECG)-isonicotinic acid complex of step f) in water immiscible solvent and filtering,
h) slurrying the obtained partially purified hydrated gallated epicatechins (EGCG & ECG)-isonicotinic acid complex of step g) in water miscible organic solvent to liberate gallated epicatechins,
i) evaporating supernatant water miscible organic solvent of step h) to dryness under reduced pressure to obtain crude residue,
j) dissolving the crude residue of step i) in water immiscible solvent,
k) treating water immiscible solvent solution of step j) with brine solution and filtering off any trace level insoluble materials,
l) concentrating water immiscible solvent solution of step k) and adding small amount of water, distilling away the water immiscible solvent to obtain concentrated aqueous solution, and
m) freeze drying the concentrated aqueous solution of step l) to obtain >97% gallated epicatechins (>75% EGCG & >20% ECG).

4. The process of claim 1, wherein the hydrated gallated epicatechins (EGCG & ECG)-isonicotinic acid complex from green tea extract or green tea dust are characterized by a XRPD pattern having peaks located at about 6.010, 6.612, 7.258, 11.646, 12.294, 14.610, 14.939, 19.229, 22.032, 26.188, 26.934, 27.433, 29.522±0.2 °2θ.

5. The process of claim 2, wherein the water miscible organic solvent is selected from methanol, ethanol, 1-propanol, 2-propanol, t-butyl alcohol, acetone, methyl butyl ketone, tetrahydrofuran, 1,4-dioxane or any mixtures thereof.

6. The process of claim 2, wherein the water immiscible organic solvents is selected from ethyl acetate, propyl acetate, butyl acetate, diethyl ether, dichloromethane, chloroform or any mixtures thereof.

* * * * *